United States Patent [19]

Wootton

[11] 4,413,002
[45] Nov. 1, 1983

[54] BRONCHODILATING HYDANTOIN DERIVATIVES

[75] Inventor: Gordon Wootton, Sawbridgeworth, England

[73] Assignee: Beecham Group Limited, England

[21] Appl. No.: 112,693

[22] Filed: Jan. 16, 1980

[30] Foreign Application Priority Data

Jan. 18, 1979 [GB] United Kingdom ............ 7901887

[51] Int. Cl.³ ............... A61K 31/415; C07D 233/78
[52] U.S. Cl. ............................ 424/273 R; 548/309; 548/313; 549/420
[58] Field of Search ............... 548/313; 424/273 R

[56] References Cited

U.S. PATENT DOCUMENTS

| | | | |
|---|---|---|---|
| 4,147,796 | 4/1979 | Wootton | 548/313 X |
| 4,152,445 | 5/1979 | Wootton | 548/313 X |
| 4,204,068 | 5/1980 | Caldwell et al. | 424/273 R |

FOREIGN PATENT DOCUMENTS

| | | |
|---|---|---|
| 2724948 | 3/1977 | Fed. Rep. of Germany ...... 548/313 |
| 2362839 | 6/1977 | France . |
| 2427331 | 5/1979 | France . |
| 2258 | 1/1978 | United Kingdom . |
| 2259 | 1/1978 | United Kingdom . |
| 1238 | 6/1978 | United Kingdom . |

*Primary Examiner*—Richard A. Schwartz
*Attorney, Agent, or Firm*—Jacobs & Jacobs

[57] ABSTRACT

Compounds of formula (I), or salts thereof:

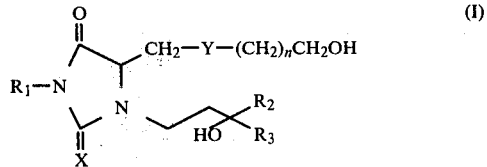

wherein:
X is oxygen or sulphur, or $>C=X$ represents

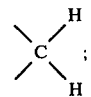

Y is $-CH_2-CH_2-$ or $-CH=CH-$;
n is 1 to 5;
$R_1$ is hydrogen or $C_{1-6}$ alkyl;
$R_2$ is hydrogen or $C_{1-4}$ alkyl; and
$R_3$ is $C_{4-9}$ alkyl, $C_{5-8}$ cycloalkyl, or $C_{5-8}$ cycloalkyl $-C_{1-6}$ alkyl; or
$R_2$ and $R_3$ taken with the carbon atom to which they are joined represent a $C_{5-8}$ cycloalkyl group, having useful pharmacological activity, pharmaceutical compositions containing them and a process for their preparation.

6 Claims, No Drawings

BRONCHODILATING HYDANTOIN DERIVATIVES

This invention relates to novel hydantoin derivatives having pharmacological activity, to a process for their preparation, to intermediates useful in that process and to pharmaceutical compositions containing them.

German Offenlegungsschrift No. 2724948 discloses that compounds of the general formula (A):

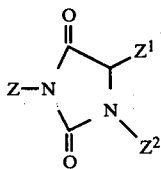

(A)

wherein:

Z is hydrogen or alkyl;

one of $Z^1$ and $Z^2$ is a group —$CH_2$—X—$X^1$—$X^2$ in which X is phenylene, —C≡C—, cis-—CH=CH— or —$CH_2$—$CQ_2$—, where each radical Q independently of the other is hydrogen or alkyl or the two radicals Q together are $C_{4-6}$ alkylene; $X^1$ is a covalent bond or a straight or branched $C_{1-6}$ alkylene chain, in which one methylene group is optionally replaced by an oxa (—O—) group, with the proviso that at least one carbon atom separates the oxa group from a —C≡C—, —CH=CH— or CO group; and $X^2$ is 5-tetrazolyl, carboxyl, carboxamide, hydroxymethylene or alkoxycarbonyl;

and the other one of $Z^1$ and $Z^2$ is a group —Y—$Y^1$—$Y^2$—$Y^3$ in which Y is —$CR_2$—$CH_2$—, where each radical R independently of the other is hydrogen or methyl; $Y^1$ is carbonyl, methylene, methylene substituted by a hydroxy group or methylene substituted by a hydroxy and an alkyl group; $Y^2$ is a covalent bond or straight-chain or branched $C_{1-7}$ alkylene optionally substituted on the carbon atom adjacent to $Y^1$ by one or two mutually independent alkyl, bicycloalkyl or cycloalkyl groups; $Y^3$ is hydrogen, hydroxy, $C_{1-7}$ alkoxy, cycloalkyl, bicycloalkyl, phenyl, benzyl, phenoxy, or benzyloxy, where each phenyl, benzyl, phenoxy or benzyloxy group may be substituted in the benzene ring by one or more hydroxy, halogen, nitro, amino, acylamino, alkenyl, alkoxy, phenyl or alkyl groups (which alkyl itself may be substituted by one or more halogens); or Y is a bond, —$CH_2$— or —$CH_2.CH_2$—, or $Y^1$, $Y^2$ and $Y^3$ together are cycloalkyl which is substituted by a hydroxy group; have pharmacological properties related to those of natural prostaglandins.

The present invention provides a class of compounds having useful pharmacological properties, which class includes a narrow group of compounds falling within the broad general disclosure of the Offenlegungsschrift, but not specifically described or suggested therein, which group has surprisingly improved bronchodilation activity relative to the compound which was specifically highlighted in the above Offenlegungsschrift for this utility.

This class of compounds of this invention is structurally distinct from the compounds of formula (B):

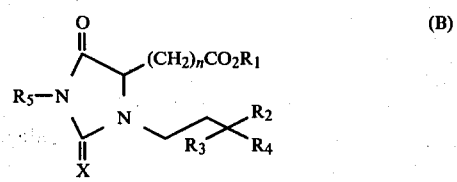

(B)

wherein:

X is O to S;

n is 1 to 8;

$R_1$ is hydrogen, or $CO_2R_1$ represents an ester group in which the $R_1$ moiety contains from 1–12 carbon atoms;

$R_2$ is hydrogen, $C_{1-4}$ alkyl, or phenyl;

$R_3$ is hydroxy or protected hydroxy;

$R_4$ is hydrogen, $C_{1-9}$ alkyl, $C_{3-8}$ cycloalkyl, $C_{3-8}$ cycloalkyl-$C_{1-6}$ alkyl, phenyl, phenyl $C_{1-6}$ alkyl, naphthyl, naphthyl-$C_{1-6}$-alkyl, any of which phenyl or naphthyl moieties may be substituted by one or more halogen, trifluoromethyl, $C_{1-6}$ alkyl, hydroxy, $C_{1-6}$ alkoxy, phenyl $C_{1-6}$ alkoxy or nitro groups; or $R_2$ and $R_4$ taken with the carbon atom to which they are joined represent a $C_{5-8}$ cycloalkyl group;

$R_5$ is hydrogen, $C_{1-6}$ alkyl, $C_{1-6}$ alkyl substituted by a nitro, hydroxy, $C_{1-6}$ alkoxy, $CO_2A$, $(CO_2A)_2$, CN or halogen group, $C_{5-8}$ cycloalkyl, phenyl, phenyl-$C_{1-6}$ alkyl, phenyl-$C_{3-6}$ cycloalkyl, any of which phenyl moieties may be substituted by one or more halogen, trifluoromethyl, $C_{1-6}$ alkyl, $C_{1-6}$ alkoxy or nitro groups; or a group $CO_2A$; in $R_5$ when present A is hydrogen or $CO_2A$ represents an ester group in which the A moiety contains from 1 to 12 carbon atoms; and salts thereof; which are disclosed in our West German Offenlegungsschrift No. 2755771 as having useful prostaglandin-like activity.

The present invention provides a compound of formula (I), or a salt thereof:

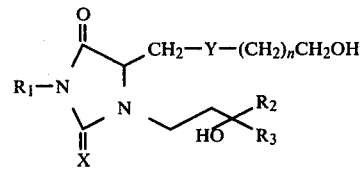

(I)

wherein:

X is oxygen or sulphur, or >C=X represents

Y is —$CH_2$—$CH_2$— or —CH=CH—;

n is 1 to 5;

$R_1$ is hydrogen or $C_{1-6}$ alkyl;

$R_2$ is hydrogen or $C_{1-4}$ alkyl; and $R_3$ is $C_{4-9}$ alkyl, $C_{5-8}$ cycloalkyl, or $C_{5-8}$ cycloalkyl —$C_{1-6}$ alkyl; or $R_2$ and $R_3$ taken with the carbon atom to which they are joined represent a $C_{5-8}$ cycloalkyl group.

It will be appreciated that compounds of the formula (I) wherein X is sulphur, or >C=X represents

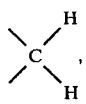

clearly fall outside the disclosure of Offenlegungsschrift No. 2724948.

Y is preferably —$CH_2$—$CH_2$— n is suitably 3 or 5, preferably 3.

When $R_1$ is an alkyl group, then it is suitably methyl or ethyl, preferably methyl. It is believed that the preferred value for $R_1$ is methyl.

Suitable examples of $R_2$ include hydrogen, methyl and ethyl. More suitably $R_2$ is hydrogen or methyl, preferably methyl.

Suitable groups $R_3$ when $R_3$ is an alkyl group include straight chain alkyl groups, such as n-butyl, n-pentyl, n-hexyl and n-heptyl, or alkyl groups branched by one or two methyl groups (at the same or different carbon atoms). Thus for example, $R_3$ may be a group $CH_2R_4$, $CH(CH_3)R_4$ or $C(CH_3)_2R_4$, wherein $R_4$ is a straight chain alkyl group such that the carbon content of the resultant group $R_3$ is 4 to 9.

In general preferred groups $R_3$ when $R_3$ is an alkyl group include straight chain pentyl, hexyl and heptyl groups. Of these, straight chain hexyl is often the most useful. Other preferred groups $R_3$ include groups $CH(CH_3)R_4$ and $C(CH_3)_2R_4$ wherein $R_4$ is straight chain butyl, pentyl or hexyl.

When $R_3$ is or contains a $C_{5-8}$ cycloalkyl moiety, the moiety may be a cyclohexyl moiety. Examples of suitable $C_{1-6}$ alkyl moieties when $R_3$ is a $C_{5-8}$ cycloalkyl-$C_{1-6}$ alkyl group include methyl, ethyl, propyl, butyl, and pentyl.

Also, $R_2$ and $R_3$ taken with the carbon atom to which they are joined can represent a $C_{5-8}$ cycloalkyl group, such as the cyclohexyl group.

The compounds of the formula (I) may form conventional salts, of the hydroxy groups or of N-$R_1$ when $R_1$ is hydrogen. Such salts include those with alkali and alkaline earth metals, more suitably sodium and potassium.

From the aforesaid it will be seen that one particularly suitable group of compounds within formula (I) is of formula (II):

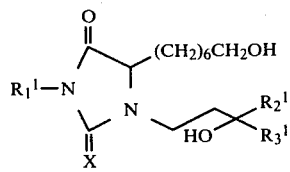

(II)

wherein:

X is as defined in formula (I);

$R^1_1$ is hydrogen or methyl;

$R^1_2$ is methyl or ethyl; and $R^1_3$ is $C_{4-9}$ alkyl; and salts thereof.

In formula (II) preferably X is oxygen.

$R^1_1$ is preferably methyl.

$R^1_2$ is preferably methyl.

Suitable and preferred straight chain and branched groups $R^1_3$ include those previously described as suitable and preferred for the group $R_3$ when $R_3$ is a $C_{4-9}$ alkyl group. Such preferred groups $R^1_3$ include straight chain pentyl, hexyl, and heptyl, and of these normally the most useful is straight chain hexyl. Other preferred groups $R^1_3$ include $CH(CH_3)R^1_4$ and $C(CH_3)_2R^1_4$ wherein $R^1_4$ is straight chain butyl, pentyl or hexyl.

A further group of compounds within formula (I) of interest is of formula (III):

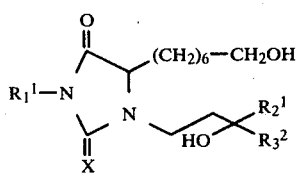

(III)

wherein:

X, $R^1_1$ and $R^1_2$ are as defined in formula (II);

$R^2_3$ is a group of formula (IV):

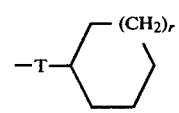

(IV)

wherein:

T is a bond, or a $C_{1-6}$ alkylene group which may be straight chain or branched by one or two methyl groups at the same or different carbon atoms; and r is 0 to 3;

and salts thereof.

In formula (III) suitable and preferred values for X, $R^1_1$ and $R^1_2$ are as described for formula (II).

In formula (IV) often T will be a group —$(CH_2)_q$— wherein q is 0 to 4. Also more suitably r is 1.

Another group of compounds within formula (I) of interest is of formula (V):

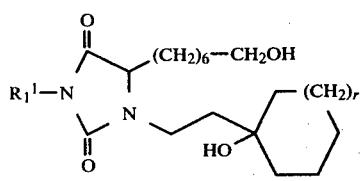

(V)

wherein: X and $R^1_1$ are as defined in formula (II), and r is as defined in formula (III).

Suitable and preferred values for the variables in formula (V) are as described in relation to formula (III).

It will of course be realised that the compounds of the formula (I) have asymmetric centres, and thus are capable of existing in a number of stereoisomeric forms. The invention extends to each of these stereoisomeric forms, and to mixtures thereof. The different stereoisomeric forms may be separated one from the other by the usual methods.

The compounds of the formula (I) have good stability.

The present invention also provides a process for the preparation of the compounds of formula (I), which process comprises the cyclisation of a compound of formula (VI):

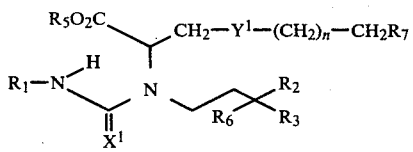

(VI)

wherein the variable groups n, $R_1$, $R_2$ and $R_3$ are as defined in formula (I);

$X^1$ is oxygen or sulphur;

$Y^1$ is $-CH_2-CH_2-$, $-CH=CH-$ or $-C\equiv C-$;

$R_5$ is a group such that $CO_2R_5$ is an ester group containing no more than twelve carbon atoms; and $R_6$ and $R_7$ are hydroxy or protected hydroxy; and thereafter if necessary converting a compound wherein $X^1$ is sulphur to the corresponding compound wherein $C=X^1$ represents

converting a compound wherein $Y^1$ is $-C\equiv C-$ to the corresponding compound wherein $Y^1$ is $-CH=CH-$, or converting a protected hydroxy group $R_6$ or $R_7$ to free hydroxy.

When $R_1$ is $C_{1-6}$ alkyl in the compound of formula (VI), then the compound of the formula (VI) is conveniently prepared in situ during the reaction of a compound of the formula (VI):

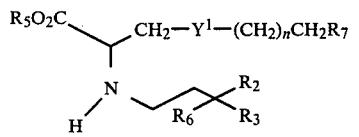

(VII)

with $R_8NCX^1$ wherein $R_8$ is $C_{1-6}$ alkyl and $X^1$ is oxygen or sulphur.

This preferred process is suitably carried out under reflux in an inert solvent such as benzene or toluene or the like. It should be stated that when in this reaction $R_8$ is a sterically hindered group then this reaction may proceed only as far as the uncyclised compound of formula (VI), in which case the necessary cyclisation of the compound (VI) can be achieved using a strong base, such as sodium hydride or sodium ethoxide, in a dry organic solvent. Sodium ethoxide in benzene, or potassium t-butoxide in toluene, benzene or hexamethyl phosphoramide are suitable reagents.

When $R_1$ is hydrogen in the compound of formula (VI), then the compound of formula (VI) is conveniently formed in situ during the reaction of a compound of formula (VII) with a salt $M^+\overline{C}NX^1$ wherein $M^+$ is a metal ion, preferably potassium, in the presence of acid. The acid for this reaction, which yields a compound of the formula (I), is suitably provided by using an acid addition salt of the compound of formula (VI), or by carrying out the reaction in aqueous acid.

The conversion of a compound of the formula (I) to another compound of the formula (I) wherein the variables are altered, when desired or necessary, may be achieved in any convenient manner.

For example compounds of the formula (I) wherein X is S may be converted to compounds wherein X is $H_2$ by reduction. This reductive desulphurisation may be carried out in the present of a suitable conventional hydrogenation catalyst, such as Raney nickel, under conventional conditions for such reactions. For example a solution of the chosen compound of the formula (I) wherein X is S is an organic solvent may be added to a refluxing suspension of the catalyst in a similar solvent.

Also, for example, if desired compounds wherein $Y^1$ is $-C\equiv C-$ may be reduced to compounds wherein Y is $-CH=C-$ in known manner. Suitably this reaction is carried out using catalytic hydrogenation, such as Lindlar catalysis. When Y is $-CH=CH-$, it may be reduced to $-CH_2-CH_2-$ in known manner, suitably using catalytic hydrogenation such as transition metal catalysis.

Similarly $R_6$ and $R^7$ protected hydroxy moieties may be deprotected in conventional manner. For example when $R_6$ is a benzyloxy group, the benzyl group may readily be removed by hydrogenolysis, and a $R_7$ tetrahydropyranyl group may be removed by acid hydrolysis.

Also $R_1$ is hydrogen compounds of the formula (I) may be converted to corresponding compounds but wherein $R_1$ is alkyl by conventional substitution reactions with $R_1L$ wherein L is a displaceable group such as a halide or other good leaving group. In such reactions it may be necessary to first convert the compound of the formula (I) to an alkali metal salt of the $R_1$ hydrogen.

It will be appreciated that $R_6$ and $R_7$ protected hydroxy compounds of the formula (I), and also compounds of the formula (I) wherein Y is $-C\equiv C-$, are useful intermediates in the preparation of the active compounds of formula (I).

Suitable examples of $R_6$ protected hydroxy groups when used include readily hydrolysable derivatives such as $C_{1-4}$ acylated hydroxy groups, such as acetoxy, and hydroxy groups etherified by readily removable inert groups such as benzyl or like groups.

While we have found that it is often unnecessary to use a $R_6$ protecting group, in contrast due to the presence of the $R_7$ hydroxy moiety in all of the numerous reactions in the preparative procedure for the intermediates of formula (VII) (as hereinafter described) we have found that most suitably $R_7$ is a protected hydroxy group. Of course the choice of a suitable protecting group for the $R_7$ hydroxy will be a routine matter to the skilled man, but we have found the use of tetrahydropyranyl to be very effective. Such protecting groups can readily be removed by acid hydrolysis.

Suitable examples of $CO_2R_5$ ester groups are $C_{1-6}$ alkyl esters such as methyl or ethyl esters.

The compounds of formula (VII) may be prepared by a process which comprises reacting a compound of formula (VIII): $H_2NCH_2CH_2CR_2R_3R_6$ with a compound of formula (IX): $R_5O_2C_1CH(Q)CH_2.Y^1.(CH_2)_n.CH_2R_7$ wherein the variable groups are as defined and Q is a good leaving group.

Suitably Q is tosylate or a halide, or like readily displaceable group. Preferably Q is bromide.

This displacement reaction occurs under conventional conditions, for example in an organic solvent in the presence of sodium carbonate, at the reflux temperature.

Compounds of formula (VIII) may be prepared in known manner.

Compounds of formula (IX) may be prepared by the de-acylation of a corresponding compound of formula (X):

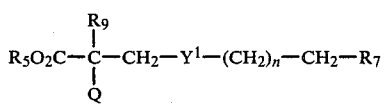

wherein $R_9$ is an acyl group containing up to 6 carbon atoms (preferably acetyl).

This de-acylation can conveniently be carried out by reaction with barium hydroxide, in an organic solvent such as dry ethanol.

The compounds of formula (X) may themselves be prepared by substitution of a corresponding compound of formula (XI):

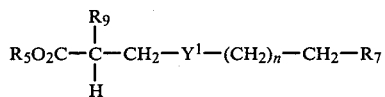

with a good leaving group.

This reaction is suitably carried out in an organic solvent such as tetrahydrofuran in the presence of a strong base such as sodium hydride. When Q is bromo in the desired compound of the formula (X), then the reaction may suitably be carried out with bromine dissolved in a suitably organic solvent such as dichloromethane, at non-extreme temperatures.

The compounds of formula (XI) may be prepared by alkylation of a compound of formula (XII): $R_5O_2\text{C}-\text{CH}_2-R_9$ with a compound of formula (XIII): $Q-\text{CH}_2-Y''-(\text{CH}_2)_n-\text{CH}_2-R_7$ wherein $Y''$ is $-\text{CH}=\text{CH}-$ or $-\text{C}\equiv\text{C}-$ and Q is a good leaving group such as a halide for example chloride.

The alkylation reaction can be carried out in conventional manner, for example in an organic solvent in the presence of a strong base such as sodium hydride at non-extreme temperatures.

It will readily be appreciated that this alkylation reaction yields compounds of formula (XI) wherein $Y'$ is $-\text{CH}=\text{CH}-$ or $-\text{C}\equiv\text{C}-$. Corresponding compounds of formula (XI) wherein $Y'$ is $-\text{CH}_2-\text{CH}_2-$ may of course be prepared therefrom in usual manner by reduction, for example with a palladium catalyst.

Alternatively, compounds of the formula (XI) wherein $Y'$ is $-\text{CH}_2-\text{CH}_2-$ may be prepared in an analogous alkylation-reduction sequence using a compound of formula (XII) and a compound of formula (XIII)':

This alternative sequence is very convenient because of the ready availability of compounds of formula (XIII)'.

It will be appreciated that the novel intermediates used in the preparation of compounds of formula (I) form an important part of this invention.

Compounds of the formula (I) have particularly useful pharmacological activity. For example compounds within the formula (I) have anti-gastric secretion activity, e.g. anti-ulcer activity, cardiovascular activity e.g. anti-hypertensive activity, platelet aggregation inhibition activity, affect the respiratory tract, e.g. bronchodilator activity, and have anti-fertility, smooth muscle and anti-arrhythmic activity.

Compounds of the formula (I) have especially useful bronchodilator activity.

In general it may be said that compounds within the formula (I) together have a range of pharmacological activities similar to those shown by the naturalprostaglandins, but that their activity profiles tend to be rather more selective so that each compound tends to have a major activity readily ascertained by routine pharmacological tests. By way of example, it has been found that many of the compounds of the formula (I) are especially useful as bronchodilator agents, such as in particular compounds of the formulae (II) and (III).

The invention therefore also provides a pharmaceutical composition comprising a compound of the formula (I) or a pharmaceutically acceptable salt thereof, and a pharmaceutically acceptable carrier.

In order to utilise the selectivity of activity found with compounds of the formula (I), normally a given compound will be used in the treatment of the disorder corresponding to the compound's major activity (that is, the disorder for which the compound has the lowest active dose) and will accordingly be formulated into the corresponding pharmaceutical composition, and administered in a manner conventional for treatment of that disorder. It may also of course be possible with compounds having one or more further pronounced activities to formulate and use the compound for those further activities as well as for the major activity, provided that there is not undesirable pharmacological interaction between the different activities, or that separation of the different activities can be obtained by a difference in the formulation or in the mode of administration.

The compositions may be in the form of tablets, capsules, powders, granules, lozenges or liquid preparations, such as oral or sterile parenteral solutions or suspension.

Tablets and capsules for oral administration may be in unit dose presentation form, and may contain conventional excipients such as binding agents, fillers, tabletting lubricants, disintegrants, and acceptable wetting agents and the like. The tablets may be coated according to methods well known in normal pharmaceutical practice. Oral liquid preparations may be in the form of, for example, aqueous or oily suspensions, emulsions, syrups, or elixirs, or may be presented as a dry product for reconstitution with water or other suitable vehicle before use. Such liquid preparations may contain conventional additives such as suspending agents, emulsifying agents, non-aqueous vehicles (which may include edible oils), preservatives, and if desired conventional flavouring or colouring agents, and the like.

For parenteral administration, fluid unit dosage forms are prepared utilising the compound of the formula (I) and a sterile vehicle. The compound, depending on the vehicle and concentration used, can be either suspended or dissolved in the vehicle. In preparing solutions the compound can be dissolved for injection and filter sterilised before filling into a suitable vial or ampoule and sealing. Advantageously, adjuvants such as a local anaesthetic, preservatives and buffering agents can be dissolved in the vehicle.

Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

When appropriate, the compositions of this invention may be presented as an aerosol for oral administration, or as a microfine powder for insufflation.

As is common practice, the compositions will usually be accompanied by written or printed directions for use in the medical treatment concerned.

It will of course be realised that the precise dosage used in the treatment of any of the hereinbefore described disorders will depend on the actual compound of the formula (I) used, and also on other factors such as the seriousness of the disorder being treated.

The invention also provides a method of treatment and/or prophylaxis of disorders in human beings or animals which comprises the administration to the sufferer of an effective amount of a compound of the formula (I). Normally however the compounds will be used in the therapy of human disorders.

The following Examples illustrate the preparation of compounds of the formula (I) and their pharmacological properties.

EXAMPLE 1(a)

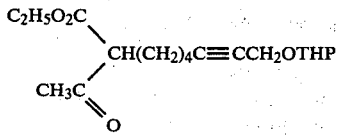

Ethyl acetoacetate (13 g; 1/10 mole) was added dropwise to a suspension of sodium hydride (3 g of 80% oil dispersion) in a mixture of dry benzene (50 ml) and dry dimethylformamide (50 ml), under nitrogen. The mixture was stirred at room temperature for 30 minutes. Sodium iodide (1.5 g) was added and then 7-chloro-hept-2-yne-1-ol-tetrahydropyranyl ether (23.1 g; 1/10 mole) was added dropwise over 30 minutes. The resulting mixture was refluxed for 3½ hours. The cooled mixture was treated with water and the organic fraction was extracted into ether. The ether solution was washed with very dilute hydrochloric acid, a trace of 5% sodium bicarbonate solution, and then with brine until the washings were neutral. The dried ether solution was evaporated in vacuo to give a yellow oil (28.8 g) which was partially distilled to removed unreacted starting materials. The residue (25.9 g) consisted of ethyl 2-acetyl-9-tetrahydropyranyloxy-non-7-ynoate.

| I.R. (cm$^{-1}$) | 1740 [$CO_2C_2H_5$]; 1710 [$COCH_3$]. |
|---|---|
| NMR ($\tau$) | 7.85 (s, 3H, C$\underline{H}_3$.CO); |
| | 6.4 (brm, 2H, OC$\underline{H}_2$); |
| | 5.85 (q, 2H, $CO_2C\underline{H}_2CH_3$); |
| | 5.75 (m, 2H, C≡CC$\underline{H}_2$O); |
| | 5.25 (bs, 1H, OC$\underline{H}$O). |

EXAMPLE 1(b)

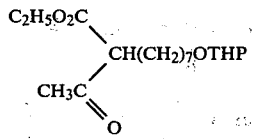

Ethyl 2-acetyl-9-tetrahydropyranyloxy-non-7-ynoate (25.9 g) was hydrogenated over 10% Pd/C (3 g) in dry dimethoxyethane (300 ml) at atmospheric pressure and room temperature. When hydrogen absorption was completed the mixture was filtered through kieselguhr and the filtrate was evaporated in vacuo. The residual oil was chromatographed on silica gel (600 g) using chloroform as eluant. Ethyl 2-acetyl-9-tetrahydropyranyloxy-nonanoate (20 g) was obtained as a colourless oil.

| NMR ($\tau$) | 7.75 (s, 3H, C$\underline{H}$, $CH_3CO$); |
|---|---|
| ($CDCl_3$) | 6.4 (brm, 4H, OC$\underline{H}_2$ × 2); |
| | 5.75 (q, 2H, $CO_2C\underline{H}_2CH_3$); |
| | 5.4 (bs, 1H, OC$\underline{H}$O). |

EXAMPLE 1(c)

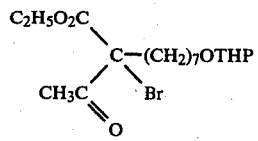

Ethyl 2-acetyl-9-tetrahydropyranyloxy-nonanoate (20 g) in dry tetrahydrofuran (100 ml) was added dropwise to a stirred suspension of sodium hydride (2.01 g of 80% oil dispersion) in dry tetrahydrofuran (50 ml), under nitrogen. The mixture was warmed to reflux for 10 minutes. The clear solution was allowed to cool to room temperature then a solution of bromine (3.15 ml) in dry dichloromethane (50 mls) was added rapidly. After stirring for 30 minutes, during which time a yellow precipitate was formed, the mixture was partitioned between water and ether. The ether solution was washed with brine, dried and evaporated in vacuo at low temperature (<30° C.). The ethyl 2-acetyl-2-bromo-9-tetrahydropyranyloxy-nonanoate was obtained as a dark yellow oil (27.1 g.) which still contained a small amount of solvent.

| NMR ($\tau$) | 7.65 (s, 3H, C$\underline{H}_3CO$); |
|---|---|
| | 6.4 (brm, 4H, OC$\underline{H}_2$ × 2); |
| | 5.75 (q, 2H, $CO_2C\underline{H}_2CH_3$); |
| | 5.5 (bs, 1H, OC$\underline{H}$O). |

EXAMPLE 1(d)

Anhydrous barium hydroxide (5.7 g) was added in portions to a stirred solution of ethyl 2-acetyl-2-bromo-9-tetrahydropyranyloxy-nonanoate (27 g) in dry ethanol (100 ml) under nitrogen. The mixture was stirred at room temperature overnight and then was filtered. The filtrate was partitioned between ether and brine and the ether solution was washed with brine, dried and evaporated to give a red oil (13.8 g). On attempted distillation, only 3.2 g of distillate was obtained before the residue began to decompose. The distillate [150° C. at 0.015 tor] was a mixture of ethyl 2-bromo-9-tetrahydropyranyloxy-nonanoate and ethyl 2-bromo-9-hydroxy-nonanoate. The mixture was dissolved in dihydropyran (10 ml) and treated with a few crystals of toluene-p-sulphonic acid. The reaction mixture was stirred at room temperature for 3 hours then was diluted with ether. The ether solution was washed with very dilute potassium hydroxide solution and with brine then was dried and evaporated in vacuo to give ethyl 2-bromo-9-tetrahydropyranyloxy-nonanoate (3.8 g) as a yellow oil.

| NMR (τ) | 6.5 (brm, OC$\underline{H}_2$ × 2); |
| --- | --- |
| | 5.9 (t, 1H, BrC$\underline{H}$CO$_2$C$_2$H$_5$); |
| | 5.8 (q, 2H, CO$_2$C$\underline{H}_2$CH$_3$); |
| | 5.5 (bs, 1H, OC$\underline{H}$O). |

EXAMPLE 1(e)

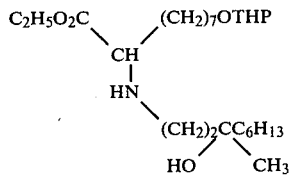

Ethyl 2-bromo-9-tetrahydropyranyloxy-nonanoate (2.5 g) and 3-hydroxy-3-methylnonylamine (2.2 g) were refluxed together in dry ethanol (50 ml) containing sodium carbonate (726 mg) overnight. The ethanol was evaporated in vacuo and the residue was partitioned between ether and brine. The ether solution was washed with brine, dried and evaporated in vacuo. The resulting yellow gum was chromatographed on silica gel (100 g) using chloroform as eluant to give ethyl 2-(3'-hydroxy-3'-methyl-n-nonyl)amino-9-tetrahydropyranyloxy-nonanoate (1.27 g) as a colourless gum.

| I.R. (cm$^{-1}$): | 3300 [OH]; 1735 [CO$_2$C$_2$H$_5$] |
| --- | --- |
| NMR (τ): | 6.8 (brm, 8H, OC$\underline{H}_2$ × 2; |
| | NC$\underline{H}_2$; NC$\underline{H}$; O$\underline{H}$); |
| | 5.85 (q, 2H, CO$_2$C$\underline{H}_2$CH$_3$); |
| | 5.5 (bs, 1H, O—C$\underline{H}$—O). |
| Mass Spectrum: | C$_{26}$H$_{52}$NO$_5$(m* + H) requires: 458.3845 |
| | found: 458.3856 |

EXAMPLE 1(f)

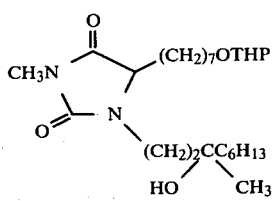

Ethyl 2-(3'-hydroxy-3'-methyl)amino-9-tetrahydropyranyloxy-nonanoate (1.19 g) was refluxed with methyl isoxyanate (148 mg) in dry toluene (30 ml) for 3 hours. The solvent was evaporated in vacuo to give a pale yellow gum (1.2 g) which was chromatographed on silica gel (36 g) using chloroform as eluant. 1-(3'-hydroxy-3'-methyl-n-nonyl)-3-methyl-5-(7"-tetrahydropyranyloxy-n-heptyl)hydantoin (950 mg) was obtained as a colourless gum.

| I.R. (cm$^{-1}$): | 3450 [OH]; 1765, 1710 [—N—$\overset{O}{\overset{\|}{C}}$—N—$\overset{O}{\overset{\|}{C}}$—] |
| --- | --- |
| NMR (γ): | 7.25 (s, 1H, O$\underline{H}$); |
| | 7.05 (s, 3H, NC$\underline{H}_3$); |
| | 6.4 (brm, 7H, OC$\underline{H}_2$×2; NC$\underline{H}_2$; NC$\underline{H}$); |
| | 5.5 (bs, 1H, OC$\underline{H}$O). |

EXAMPLE 1(g)

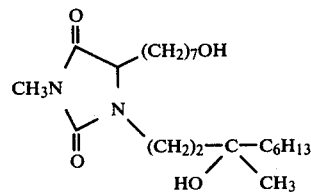

1-(3'-hydroxy-3'-methyl-n-nonyl)-3-methyl-5-(7"-tetrahydropyranyloxy-n-heptyl)hydantoin (950 mg) was stirred overnight at room temperature, with 5 N sulphuric acid (5 ml) and methanol (20 mls). The methanol was evaporated in vacuo at room temperature and the residue was extracted with ether. The ether solution was washed with 5% sodium bicarbonate solution and with brine then was dried and evaporated to give 1-(3'-hydroxy-3'-methyl-n-nonyl)-3-methyl-5-(7"-hydroxy-n-heptyl)hydantoin (Compound 1) (640 mg) as a pale yellow gum.

| I.R. (cm$^{-1}$): | 3430 [OH]; 1760, 1700 [—N.$\overset{O}{\overset{\|}{C}}$.N.$\overset{O}{\overset{\|}{C}}$—] |
| --- | --- |
| NMR (γ): | 7.5 (s, 2H, OH×2); |
| (CDCl$_3$) | 7.0 (s, 3H, NCH$_3$); |
| | 6.6 (brm, 2H, NCH$_2$); |
| | 6.4 (t, 2H, CH$_2$OH); |
| | 5.95 (t, 1H, NCH). |
| Mass Spectrum: | C$_{21}$H$_{40}$N$_2$O$_4$(m*) requires: 384.2988 |
| | found: 384.3002 |

EXAMPLE 2(a)

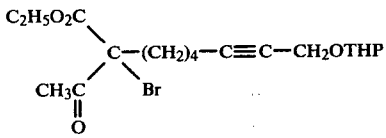

In a similar manner to Example 1c, ethyl 2-acetyl-2-bromo-9-tetrahydropyranyloxy-non-7-ynoate was prepared from ethyl 2-acetyl-9-tetrahydropyranyloxy-non-7-ynoate and bromine.

EXAMPLE 2(b)

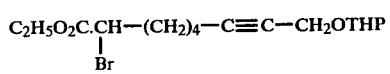

In a similar manner to that of Example 1d, ethyl 2-bromo-9-tetrahydropyranyloxy-non-7-ynoate was prepared from ethyl 2-acetyl-2-bromo-9-tetrahydropyranyloxy-non-7-ynoate.

EXAMPLE 2(c)

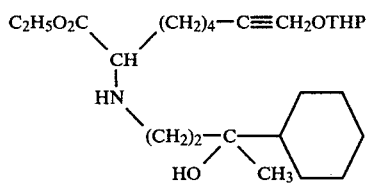

In a similar manner to that of Example 1e, ethyl 2-(3'-hydroxy-3'-cyclohexyl-n-butyl)amino-9-tetrahydropyranyloxy-non-7-ynoate was prepared from ethyl 2-bromo-9-tetrahydropyranyloxy-non-7-ynoate and 3-hydroxy-3-cyclohexyl-n-butylamine.

EXAMPLE 2(d)

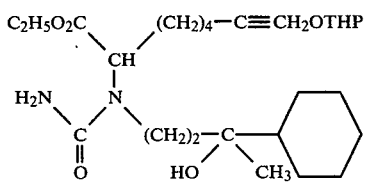

Hydrochloric acid (2.5 ml of 1N) was added dropwise to an ice cold solution of ethyl 2-(3'-hydroxy-3'-cyclohexyl-n-butyl)amino-9-tetrahydropyranyloxy-non-7-ynoate (1 g) in ethanol (2.5 ml). The mixture was stirred for ½ hour. Potassium cyanate (0.18 g; 1 eq.) in water (2 ml) was added dropwise to the ice cold solution. The resulting white suspension was stirred at room temperature overnight, the mixture was partitioned between water and ether, and the ether solution was washed with brine, dried and evaporated in vacuo to give ethyl 2-[N-(3'-hydroxy-3'-cyclohexyl-n-butyl)-N-formamido]amino-9-tetrahyropyranyloxy-non-7-ynoate (1.18 g) as a yellow gum.

EXAMPLE 2(e)

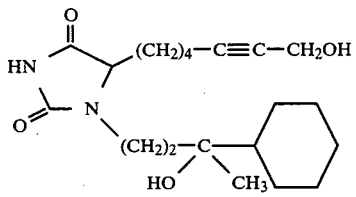

Ethyl 2-[N-(3'-hydroxy-3'-cyclohexyl-n-butyl)-N-formamido]amino-9-tetrahydropyranyloxy-non-7-ynoate (1.8 g) was heated at about 100° C. for 3 hours to give a mixture of 1-(3'-hydroxy-3'-cyclohexyl-n-butyl)-5-(7''-tetrahydropyranyloxy-n-non-5''-yne)hydantoin (about 70%) and 1-(3'-hydroxy-3'-cyclohexyl-n-butyl)-5-(7''-hydroxy-non-5''-yne)hydantoin (about 30%) (1 g). The mixture was stirred in methanol (5 ml) with 5 N sulphuric acid (1 ml) overnight. The reaction mixture was diluted with ether (50 ml) and the ether solution was washed with 5% sodium bicarbonate solution and with brine then was dried and evaporated in vacuo to give impure 1-(3'-hydroxy-3'-cyclohexyl-n-butyl)-5-(7''-hydroxy-non-5''-yne)hydantoin.

| IR (cm$^{-1}$): | 3400 (OH); 3175 (NH) |
|---|---|
| | 1760, 1700 (hydantoin ring) |

EXAMPLE 3(a)

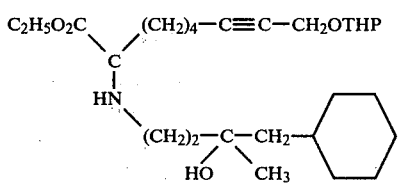

In a similar manner to that of Example 2c, ethyl 2-(3'-hydroxy-3'-methyl-4'-cyclohexyl-n-butyl)amino-9-tetrahydropyranyloxynon-7-ynoate was prepared from ethyl 2-bromo-9-tetrahydropyranyloxynon-7-ynoate and 3-hydroxy-3-methyl-4-cyclohexyl-n-butylamine.

EXAMPLE 3(b)

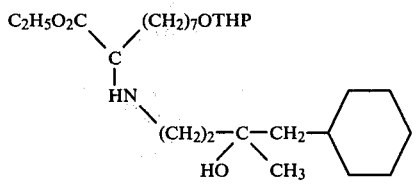

Ethyl 2-(3'-hydroxy-3'-methyl-4'-cyclohexyl-n-butyl)amino-9-tetrahydropyranyloxy-non-7-ynoate (7 g) was hydrogenated over 10% Pd/C (1.4 g) in dry dimethoxyethane (100 ml) at atmospheric pressure and room temperature. When hydrogen absorption was completed, the mixture was filtered through Kieselguhr, and the filtrate was evaporated in vacuo to give ethyl 2-(3'-hydroxy-3'-methyl-4'-cyclohexyl-n-butyl)amino-9-tetrahydropyranyloxy-nonanoate (7 g) as a pale yellow oil.

EXAMPLE 3(c)

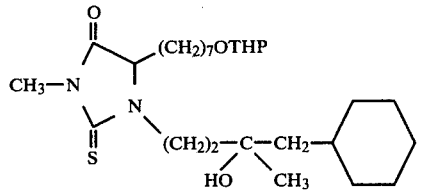

Ethyl 2-(3'-hydroxy-3'-methyl-4'-cyclohexyl-n-butyl)amino-9-tetrahydropyranyloxynonanoate (3.5 g) was refluxed with methyl isothiocyanate (0.55 g) in dry toluene (100 ml) for 3 hours. The solvent was evaporated in vacuo to give 1-(3'-hydroxy-3'-methyl-4'-cyclohexyl-n-butyl)-3-methyl-5-(7''-tetrahydropyranyloxy-n-heptyl)-2-thiohydantoin (3.4 g) as a yellow gum.

EXAMPLE 3(d)

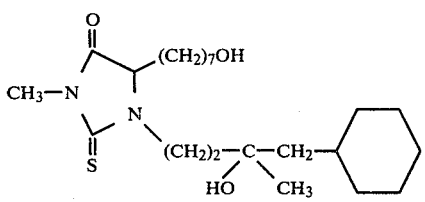

1-(3'-Hydroxy-3'-methyl-4'-cyclohexyl-n-butyl)-3-methyl-5-(7''-tetrahydropyranyloxy-n-heptyl)-2-thiohydantoin (3.4 g) in methanol (24 ml) was stirred overnight, at room temperature, with 5 N sulphuric acid (4.9 ml). The methanol was evaporated in vacuo and the residue was extracted with ether. The ether solution was washed with 5% sodium bicarbonate solution and with brine then was dried and evaporated in vacuo to give impure 1-(3'-hydroxy-3'-methyl-4'-cyclohexyl-n-butyl)-3-methyl-5-(7''-hydroxy-n-heptyl)-2-thiohydantoin (2.4 g) as a yellow gum.

| NMR | ($\tau$, CCl$_4$) 7.4, bf, 2H (OH × 2); 6.85, s, 3H (NCH$_2$); 6.6, m, (CH$_2$OH). |
|---|---|
| IR (cm$^{-1}$) | 3400 ($\overline{OH}$); 1740 (C=O) |

PHARMACOLOGICAL DATA

Bronchodilator Activity

The compounds were examined for their ability to inhibit 5-hydroxytryptamine induced bronchoconstriction in the anaesthetised, artificially respired guinea pig (Konzett-Rossler preparation). The compounds were administered intravenously.

The Compound 1 had an ED$_{50}$ of 0.88 μg/kg.

In complete contrast, the compound specifically highlighted in Offenlegungsschrift No. 2724948 for its bronchodilator activity, namely 5-(6-carboxyhexyl)-1-(3-hydroxy-4,4-dimethyloctyl) hydantoin, was found to have an ED$_{50}$ in this test of 24.6 μg/kg.

This shows that Compound 1 is at least an order of magnitude more potent a bronchodilator than the stated prior art compound.

What we claim is:

1. A compound selected from the group consisting of an alcohol of the formula:

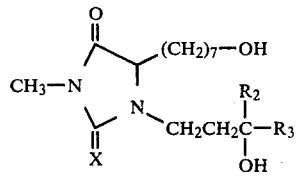

and the pharmaceutically acceptable salts thereof wherein
X is oxygen or sulfur;
R$^2$ is methyl or ethyl; and
R$^3$ is alkyl of 4 to 9 carbon atoms or a group of the formula:

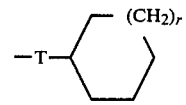

in which T is a carbon-carbon bond or methylene and r has a value of 0 to 3.

2. A compound according to claim 1 wherein R$_3$ is cyclohexyl or cyclohexylmethyl.

3. A compound according to claim 1, wherein R$_3$ is straight chain pentyl, hexyl or heptyl.

4. 1-(3'-hydroxy-3'-methyl-n-nonyl)-3-methyl-5-(7''-hydroxy-n-heptyl)hydantoin.

5. A pharmaceutical composition for the treatment or prophylaxis of bronchoconstriction comprising an effective amount of a compound according to claim 1 together with a pharmaceutically acceptable carrier.

6. A pharmaceutical composition according to claim 5 wherein said compound is 1-(3'-hydroxy-3'-methyl-n-nonyl)-3-methyl-5-(7''-hydroxy-n-heptyl) hydantoin.

* * * * *